(12) United States Patent
Milton

(10) Patent No.: US 6,342,326 B1
(45) Date of Patent: Jan. 29, 2002

(54) SYNTHESIS AND USE OF ACYL FLUORIDES OF CYANINE DYES

(75) Inventor: Raymond C. Milton, La Habra, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 09/568,446

(22) Filed: May 10, 2000

(51) Int. Cl.[7] .................. G03G 15/08; G03C 1/005; G01N 33/554; C07D 209/56; C07H 21/00
(52) U.S. Cl. .................. 430/93; 435/6; 430/581; 436/519; 536/25.32; 548/427
(58) Field of Search ................. 435/6; 430/93, 430/581; 436/519; 536/25–32; 548/427

(56) References Cited

U.S. PATENT DOCUMENTS

| | | | |
|---|---|---|---|
| 4,337,063 A | 6/1982 | Mihara et al. | 23/230 B |
| 4,404,289 A | 9/1983 | Masuda et al. | 436/538 |
| 4,405,711 A | 9/1983 | Masuda et al. | 435/4 |
| 4,414,325 A | 11/1983 | Masuda et al. | 435/7 |
| 4,981,977 A | 1/1991 | Southwick et al. | 548/455 |
| 5,360,928 A | 11/1994 | Carpino et al. | 562/849 |
| 5,569,587 A | * 10/1996 | Waggoner | 435/6 |
| 5,627,027 A | 5/1997 | Waggoner | 435/6 |
| 6,110,630 A | * 8/2000 | Reddy et al. | 430/93 |

OTHER PUBLICATIONS

Wong et al. "Specific reaction of 9–cis–retinoyl fluoride with bovine opsin" Biochemistry, vol. 23, pp. 20–27, 1984.*
Joseph Miller, et al., "Halogen Mobility in $S_N2$ Reactions of Carbonyl Compounds. Comparison with Aromatic Halogen Mobility," J. Chem. Soc. Perkin Trans. II, pp. 323–327, 1985.
Richard E. Motie, et al., "The Bronsted Acid–Catalysed Hydrolysis of Acyl Fluorides in Aqueous Media; Evidence for Two Mechanism," J. Chem. Soc. Perkin Trans 2, pp. 859–860, 1992.
Maria Jedrzejczak, et al., "The Kinetics of Aminolysis of Acyl Halides," J. Chem. Soc. Perkin Trans. 2, ppp. 599–600, 1993.

* cited by examiner

Primary Examiner—Jezia Riley
(74) Attorney, Agent, or Firm—William H. May; Arnold Grant

(57) ABSTRACT

This invention provides dyes, particularly cyanine and related dyes, with acyl fluoride activating groups, the dyes having the general formula

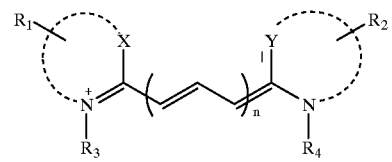

wherein:

each dotted line represents carbon atoms necessary to form a fused substituted or unsubstituted aromatic ring;

n is an integer selected from the group consisting of 1, 2 and 3;

X and Y are selected from the group consisting of S, O, N, $CH_2$ and $C(CH_3)_2$;

at least one of said $R_1$ and $R_2$ comprises a sulfonic acid or sulfonate group attached to the aromatic ring; and $R_3$ and $R_4$ are independently selected from the group consisting of alkylcarboxylate, activated alkylcarboxylate and an inert group; wherein at least one of said $R_3$ and $R_4$ groups is alcylcarboxylate or activated alkylcarboxylate with the carboxyl group converted to an acyl fluoride. The inert group is a group that is inert towards acyl fluoride and has a sterical structure which allows aminoacylation of the acyl fluoride group.

39 Claims, 5 Drawing Sheets

TEST:
BIOTINYLATED H-ras TARGET

SYNTHESIS AND USE OF ACYL FLUORIDES OF CYANINE DYES

BACKGROUND OF THE INVENTION

1. Area of the Art

The invention relates generally to activated dyes and specifically to activated cyanine dyes with an acyl fluoride activating group, their synthesis and methods of use in labeling of biopolymers.

2. Description of the Prior Art

Many procedures employed in biomedical research and recombinant DNA technology rely heavily on the use of nucleotide or polynucleotide derivatives radioactively labeled with isotopes. However, the rapidly increasing costs of radioactive waste disposal, together with an increased awareness of the potentially harmful effects of exposure to radiation, have contributed to shifting the emphasis toward other ways of labeling synthetic oligonucleotides. Although many different types of non-radioactive labels have found their use in biological detection assays, use of fluorescent labels has expanded rapidly in recent years due to both improvements in detection instrumentation and to the increased number of novel fluorescent labeling reagents.

The sensitivity and accuracy of fluorescence detection techniques are dependent on the physical and chemical characteristics of the dyes they employ. A common problem with many commercially available fluorescent labeling reagents is that they are not water-soluble and must be dissolved in organic solvents prior to substrate labeling in aqueous media. Such organic solvents can have a deleterious effect upon sensitive substrates. Another problem related to the dye's chemical structure is non-specific staining of cellular matter by the dye, which reduces signal to noise ratio during observation.

One of the major issues related to fluorescent labeling of oligonucleotides is the availability of fluorescent dyes in one or another chemical form. Ideally, the chosen fluorescent dye would be available as a fully protected, modified phosphoramidite for direct labeling during DNA synthesis. However, phosphoramidites are substantially more expensive and less stable than their standard, unmodified counterparts. Consequently, an indirect labeling method is used when the chosen fluorescent dye is not available as a modified phosphoramidite. The indirect method requires reacting an activated fluorescent dye with a nucleotide or oligonucleotide into which a primary amino group has been incorporated, usually at the 5' end. Therefore, a selectivity towards nitrogen nucleophiles is a highly desirable property of fluorescent dyes employed in indirect labeling of oligonucleotides.

Cyanine and related dyes offer many advantages over existing fluorescent labeling reagents. These dyes strongly absorb fluorescent light. Many cyanine and related dyes are relatively photo-stable and do not rapidly bleach under the fluorescence microscope. They can be covalently attached to biological and non-biological markers to make these materials fluorescent. By synthesizing structural modifications of the chromophore portion of cyanine dyes, different fluorescent labeling reagents absorbing and emitting in a broad spectrum range from 400 to nearly 1100 nm can be obtained.

Thus, reactive derivatives of these dyes can be made for assays that require simultaneous measurement of a number of labeled materials. Additionally, due to their relatively small size, cyanine dyes minimally perturb the function of the labeled product. Finally, the versatility of functional groups that can be incorporated into cyanine dyes permits control over the solubility of the dye and labeled product and helps reduce non-specific binding of the labeled materials to irrelevant components in an assay mixture (Waggoner, U.S. Pat. No. 5,569,587 and U.S. Pat. No. 5,627,027).

In order to improve covalent attachment of cyanine dyes to target molecules, techniques for activating cyanine dyes by the incorporation of a reactive functional group (or activating group) have been developed. Waggoner (U.S. Pat. No. 5,569,587 and U.S. Pat. No. 5,627,027) has presented numerous cyanine dye derivatives that can be used as covalently reacting molecules. The reactive groups used in these dyes are isothiocyanate, isocyanate, monochlorotriazine, dichlorotriazine, mono-or di-halogen substituted pyridine, mono- or di-halogen substituted diazine, aziridine, sulfonyl halide, acid halide (except for fluorides), hydroxysuccinimide ester, hydroxy sulfosuccinimide ester, imido ester, glyoxal and aldehyde. However, these types of cyanine dyes exhibit little or no selectivity towards nitrogen nucleophiles over competing species such as water or hydroxyl groups and, therefore, are not effective in labeling amino-modified materials such as amino-oligonucleotides.

The incorporation of carboxylic groups into the basic cyanine structure to increase solubility of the dye in water and to permit fluorescent labeling through the use of derived active esters has been suggested by Waggoner (U.S. Pat. No. 4,981,977 and U.S. Pat. No. 5,627,027). Miraha et al. (U.S. Pat. No. 4,337,063) and Masuda et al. (U.S. Pat. No. 4,404,289; U.S. Pat. No. 4,405,711; U.S. Pat. No. 4,414,325) have synthesized a variety of cyanine dyes with carbodiimides, anhydrides, active esters and other activating groups. These patents show that these reagents can be used as photographic sensitizers. However, most of the dyes mentioned in those patents are only weakly fluorescent. They are not especially photostable, and their solubility properties are not optimal for many uses that would involve fluorescence detection of labeled materials. Moreover, these dyes also lack selectivity towards nitrogen nucleophiles.

In summary, existing chemistries for attaching cyanine dyes to nucleotides and oligonucleotides exhibit little or no selectivity towards nitrogen nucleophiles over competing species such as water or hydroxyl groups. In addition, the existing methodologies are generally complicated, expensive, and produce undesirable organic by-products. Therefore, a need exists for novel methods of activating fluorescent dyes which overcome the difficulties of the prior art. A need also exists for methods of labeling nucleotides and oligonucleotides in both organic and aqueous solvents.

SUMMARY OF THE INVENTION

The present invention is based on the discovery that an acyl fluoride group incorporated into a cyanine dye structure provides desirable selectivity towards nitrogen nucleophiles. Fluorine is a halogen with unique physical and chemical properties such as, for instance, its ability to react with some of the noble gasses. Similarly, fluorides have strikingly different properties from the other halides. Amino acid fluorides are known as effective reagents for peptide coupling due to their selective reactivity towards amino groups (Carpino et al., U.S. Pat. No. 5,360,928). Fluorides, however, have never been suggested by the prior art as a desirable activating group of cyanine dyes. It is a surprise discovery of the present invention that cyanine dyes activated by acyl fluoride groups have specific reactivity towards nitrogen nucleophiles compared to oxygen nucleophiles, while remaining stable in aqueous solutions under labeling conditions.

One aspect of the present invention provides an activated dye having the formula:

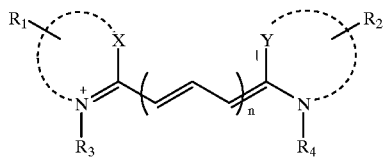

wherein each dotted line represents carbon atoms necessary to form a fused substituted or unsubstituted aromatic ring; n is an integer selected from the group consisting of 1, 2 and 3; X and Y are selected from the group consisting of S, O, N, $CH_2$, and $C(CH_3)_2$; at least one of said $R_1$ and $R_2$ comprises a sulfonic acid or sulfonate group attached to the aromatic ring; and $R_3$ and $R_4$ are independently selected from the group consisting of alkylcarboxylate, activated alkylcarboxylate and an inert group; wherein at least one of the $R_3$ and $R_4$ groups is alcylcarboxylate or activated alkylcarboxylate with carboxyl group converted to an acyl fluoride and wherein the inert group is a group that is inert towards acyl fluoride and has a sterical structure which allows aminoacylation of the acyl fluoride group. The inert group may be selected from the group consisting of alkanes, alkenes, dienes, alkynes, arenes, ketones, amides and ethers. When necessary to improve stability, the alkyl carbon adjacent to the acyl fluoride group may also be substituted with a substituent group that is neither reactive nor sterically hinders aminoacylation.

Particularly, the present invention relates to cyanine dyes with acyl fluoride(s) activating group(s). According to one embodiment of the present invention, the cyanine dye is selected from the group consisting of Cy5, benzyl Cy5, dibenzyl Cy5, Cy7 benzyl Cy7, and dibenzyl Cy7.

Another aspect of the present invention provides a method of activating a dye by substituting the hydroxyl of a carboxylic group of the dye with fluorine. The method includes the steps of:

(a) providing a dye having at least one carboxylic group;
(b) providing a fluorinating reagent capable of reacting with the carboxylic group of said dye to form acyl fluoride; and
(c) reacting said dye with said fluorinating agent under a condition sufficient for formation of at least one acyl fluoride group.

According to embodiments of the present invention, the dye can be a cyanine dye, and particularly Cy5, benzyl Cy5, dibenzyl Cy5, Cy7, benzyl Cy7 or dibenzyl Cy7. The fluorinating agent may be diethylaminosulfur trifluoride (DAST), cyanuric fluoride or tetramethylfluoroformadinium hexafluorophosphate (TFFH) or any other fluorinating agent depending on the methodology used.

A further aspect of the present invention provides a method wherein luminescent dyes, which contain an acyl fluoride group, are used to label biological and non-biological materials at their amine site. The method includes the steps of (a) providing an activated dye with at least one acyl fluoride group;
(b) providing a material containing a nitrogen nucleophile; and
(c) reacting said dye with said material under a condition sufficient to couple the dye to the material.

According to embodiments of the present invention, the dye can be a cyanine dye, and particularly Cy5, benzyl Cy5, dibenzyl Cy5, Cy7, benzyl Cy7 and dibenzyl Cy7. The materials may be polymers, DNA, drugs, toxins, cells, microbial materials, particles, proteins, amino-modified nucleic acids, combinations thereof and, particularly, amino-modified oligonucleotides. The dyes of this invention are advantageously soluble in an aqueous medium and allow a simple one-step labeling process.

The present invention provides both economic and technical advantages over the use of other activating groups in the labeling of biopolymers, and especially amino-modified oligonucleotides. The acyl fluoride group allows for fast reaction kinetics of cyanine dyes with target biopolymers which results in only a trace amount of hydrogen fluoride which is instantly neutralized by a reaction buffer. Thus, introduction of an acyl fluoride group into cyanine dyes simplifies and reduces the cost of their application and handling.

DESCRIPTION OF THE FIGURES

The above-mentioned and other features of this invention and the manner of obtaining them will become more apparent, and will best be understood, by reference to the following description, taken in conjunction with the accompanying drawings. These drawings depict only a typical embodiment of the invention and do not therefore limit its scope. They serve to add specificity and detail, in which.

DETAILED DESCRIPTION OF THE INVENTION

Figure 1:
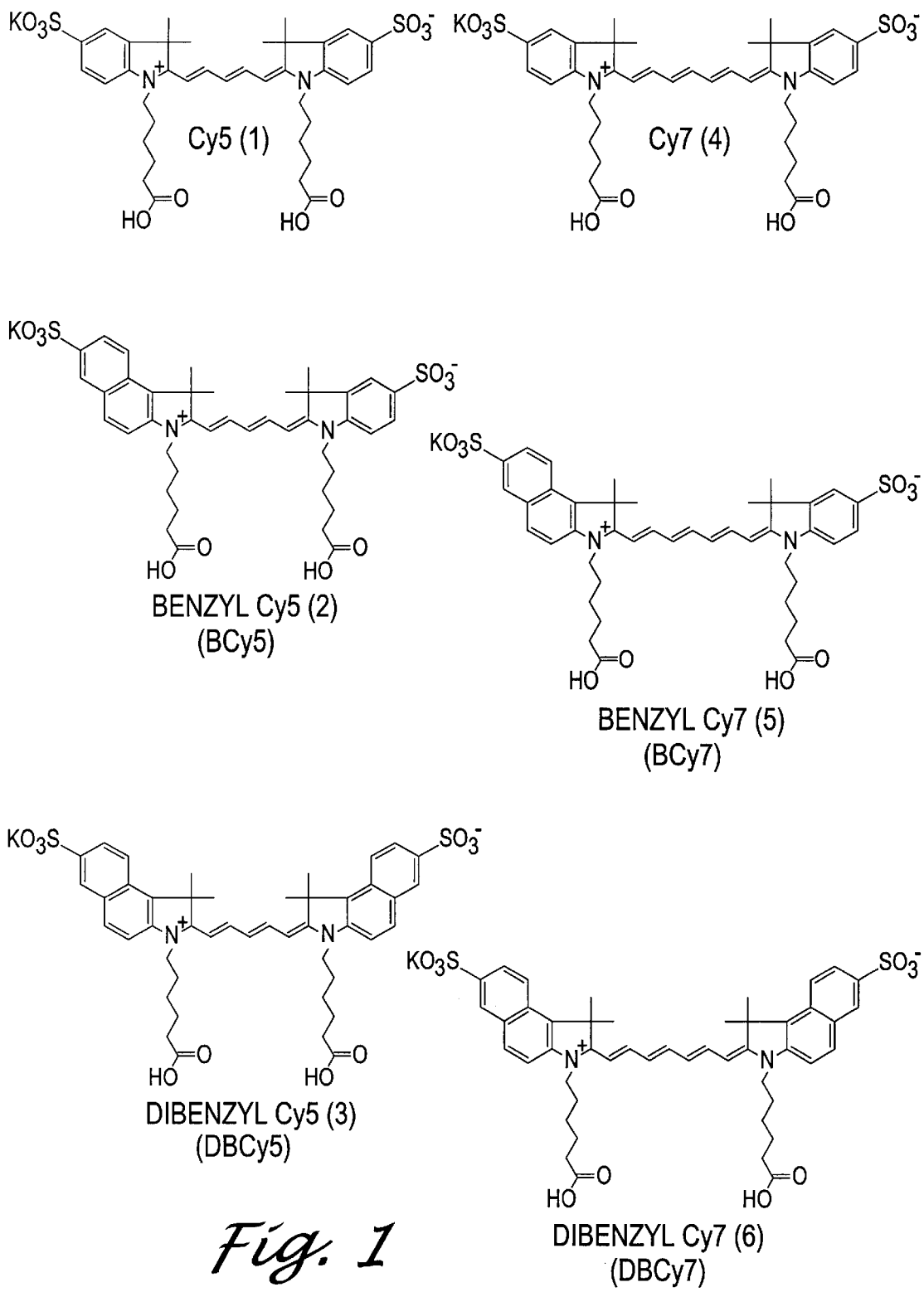
FIG. 1 shows structural formulas of some cyanine dyes.

The present invention provides an activated dye having a general formula:

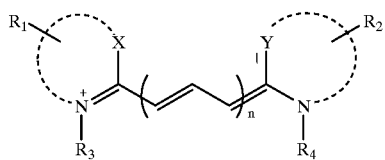

wherein:
- each dotted line represents carbon atoms necessary to form a fused substituted or unsubstituted aromatic ring;
- n is an integer selected from the group consisting of 1, 2 and 3;
- X and Y are selected from the group consisting of S, O, N, $CH_2$ and $C(CH_3)_2$;
- at least one of said $R_1$ and $R_2$ groups comprises a sulfonic acid or sulfonate group attached to the aromatic ring; and
- $R_3$ and $R_4$ are independently selected from the group consisting of alkylcarboxylate, activated alkylcarboxylate and an inert group; wherein at least one of the $R_3$ and $R_4$ groups is alcylcarboxylate or activated alkylcarboxylate with carboxyl group converted to an acyl fluoride.

For the purpose of the present invention, an inert group is a group that is inert towards acyl fluoride and has a sterical structure which allows aminoacylation of the acyl fluoride group. Examples of an inert group of the present invention include, but are not limited to alkanes, alkenes, dienes, alkynes, arenes, ketones, amides, and ethers.

When necessary to improve stability, the alkyl carbon adjacent to the acyl fluoride group may also be substituted with a substituent group that is neither reactive nor sterically hinders aminoacylation. Examples of such substituent groups include, but are not limited to, alkyl, aryl, amide or a reactive group that is blocked by a suitable protecting group.

The activated dyes can contain a heterocyclic ring, a single ring aromatic structure, such as a phenyl ring, or a fused ring structure, such as a naphthyl ring. While it is required that at least one $R_3$ or $R_4$ group is acyl fluoride, both $R_3$ and $R_4$ groups can be acyl fluorides. Alkyl groups of the activated dye generally possess one to twelve carbon atoms. For the purposes of increasing water solubility, reducing unwanted nonspecific binding or reducing the interactions between two or more reactive chromophores, $R_1$, $R_2$, $R_3$, and $R_4$ groups can be independently selected from the well-known polar and electrically charged chemical groups. However, it is required that at least one of the $R_1$ and $R_2$ groups is a sulfonic acid or a sulfonate group and at least one of the $R_3$ or $R_4$ groups is acyl fluoride.

Generally speaking, the dyes of the present invention can be any of the fluorescent dyes commonly used for labeling purposes as long as they incorporate at least one acyl fluoride group. The absorption and emission wavelengths of the dye are not restricted to a particular region of the spectrum but may be anywhere from the near UV through the near IR region or beyond these extremes. According to embodiments of the present invention, the dyes may be cyanine and related dyes.

Cyanine dyes have several desirable properties to serve as sensitive detection labels, including absorption at longer wavelengths (which translates into the use of inexpensive detection systems and low background from biological samples at these wavelengths), high extinction coefficient, relatively high quantum efficiency, small molecular size, ease of chemical manipulation without compromising the fluorescence characteristics and reasonable stability to reagents, pH and temperature.

The cyanine dyes have a general structure where the chromophore of the cyanine dyes is composed of a series of conjugated double bonds having two quaternary nitrogen atoms at the terminal ends which share one positive charge. According to the number of central double bonds, the cyanine dyes can be classified as monocarbocyanine (n=1, also known as trimethinecarbocyanine), dicarbocyanine (n=2, also known as pentamethinecarbocyanine), and tricarbocyanine (n=3, also known as heptamethinecarbocyanine). The number of central double bonds determines in part the excitation color. Often, higher values of n contribute to increased luminescence and absorbance. At values of n above 4, the compound becomes unstable. Thereupon, further luminescence can be imparted by modifications at the ring structures. When n=2, the excitation wavelength is about 650 nm and the compound is very fluorescent.

An alkyl chain terminated with a chemically reactive group such as alkyl, alkylsulfonate or alkylcarboxylate, can be attached to the nitrogen in the indole or benzoindole portion of the dye. The incorporation of at least one reactive functional group, such as the carboxylate or sulfonate group, into the basic cyanine structure permits covalent attachment of the dye to a nucleotide through the use of derived active esters. The length of the attached alkyl chain is preferably about 1 to 12 carbon atoms long. The most practical alkyl chain length is about 6 carbon atoms long.

In one embodiment of this invention, activated dyes are acyl fluorides of cyanine dyes shown in FIG. 1. The first set of dyes, Cy5(1), BCy5(2) and DBCy5(2), are dicarbocyanine dyes, while the second set of dyes, Cy7(4), Bcy7(5) and DBCy7(6), are tricarbocyanine dyes. The difference between the two sets of dyes is the presence of an additional double bond in Cy7(4), Bcy7(5) and DBCy7(6) relative to Cy5(1), Bcy5(2) and DBCy5(3), respectively Consequently, the dicarbocyanine dyes have absorption and emission maxima about 100 nm shorter than their tricarbocyanine counterparts. The benzoindole cyanines, benzyl Cy5 (BCy5) and benzyl Cy7 (BCy7), have one benzene group substitution and dibenzyl Cy5 (DBCy5) and dibenzyl Cy7 (DBCy7) have two extra benzene group substitutions relative to the corresponding indole cyanines, Cy5 and Cy7. As such, benzoindole cyanines have absorption and emission maxima longer than their indole counterparts. Cy5 and Cy7 are commercially available from Amersham and BDL. Alternatively, cyanine dyes can be synthesized de novo, as previously described (R. J. Mujumder et al., *Bioconjugate Chemistry*, 4(2):105 (1993); and S. R. Mujumder et al., *Bioconjugate Chemistry*, 7(2):356 (1996); both of which are incorporated herein by reference).

Many dye molecules, and particularly cyanine dye molecules, tend to form aggregates in aqueous solution, particularly when inorganic salts are present, as in buffered solutions and physiological salines. These aggregates usually have absorption bands shifted to the short wavelength side of the monomer absorption and are generally very weak fluorescent species. It has been found that the arylsulfonate dyes, having a sulfonate group attached to an aromatic ring structure of the dye, have a minimal tendency to form these aggregates. The sulfonate groups attached to an aromatic ring structure of the dyes have little or no effect on the chromophore, but do increase the photostability, water solubility and charge density of the molecules. The term sulfonate is meant to include sulfonic acid, because the sulfonate group is merely ionized sulfonic acid.

This invention requires dyes to be modified (or activated) by incorporating into the molecule a reactive acyl fluoride group which is selectively reactive with amine groups on proteins and other materials for purposes of fluorescence detection of those materials. Fluorine is a unique element of the periodic table, having, for instance, the ability to react with some of the noble gasses. It has properties distinctively different from other halogens and out of line with the trend in the halogen group of the Periodic Table. For example, while being the most electronegative element, due to its small size and resulting strong repulsion between the valence electrons, fluorine has electron affinity lower than that of chlorine. The incorporation of fluorine into carbon-containing moieties, such as the carboxyls of cyanine dyes, brings about significant changes in their chemical activity and reaction kinetics. Due to the singular way the fluorine atom shares electrons in the carbon-fluorine bond, as well as its relative size and ionization energy, acyl fluorides, unlike other acyl halides, are selective towards nitrogen nucleophiles over competing species such as oxygen nucleophiles and, therefore, are relatively resistant to water. Additionally, the small size of the fluorine atom obviates steric hindrance in the formation of an amide bond. On the contrary, other reactive groups, including other halogens, often create steric hindrance and thus slow down the reaction. Therefore, the specific reactivity of acyl fluorides for their targets, combined with heir stability in aqueous conditions, is unexpected and different from other acyl halides.

Another aspect of the present invention provides a method for activating a dye. The method comprises the steps of:
(a) providing a dye having at least one carboxylic group;
(b) providing a fluorinating reagent capable of reacting with the carboxylic group of said dye to form an acyl fluoride; and
(c) reacting said dye with said fluorinating agent under a condition sufficient to form a dye with at least one acyl fluoride group.

A wide range of dyes containing at least one carboxylic group may be used in the present invention. For example, dyes of the following general formula can be used:

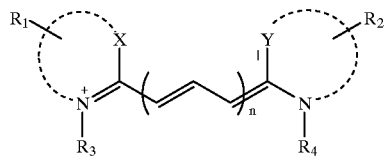

wherein:

each dotted line represents carbon atoms necessary to form a fused substituted or unsubstituted aromatic ring;

n is an integer selected from the group consisting of 1, 2 and 3;

X and Y are selected from the group consisting of S, O, N, $CH_2$ and $C(CH_3)_2$;

at least one of said $R_1$ and $R_2$ comprises a sulfonic acid or sulfonate group attached to the aromatic ring; and $R_3$ and $R_4$ are independently selected from the group consisting of alkylcarboxylate, activated alkylcarboxylate and an inert group; wherein at least one of the $R_3$ and $R_4$ groups is alcylcarboxylate or activated alkylcarboxylate with carboxyl group converted to an acyl fluoride and wherein the inert group is a group that is inert towards acyl fluoride and has a sterical structure which allows aminoacylation of the acyl fluoride group. The inert group may be selected from the group consisting of alkanes, alkenes, dienes, alkynes, arenes, ketones, amides, and ethers.

The dyes can contain a heterocyclic ring, a single ring aromatic structure, such as a phenyl ring, or a fused ring structure, such as a naphthyl ring. While it is required that at least one $R_3$ Of $R_4$ group is alkylcarboxylate, both $R_3$ and $R_4$ groups can be alkylcarboxylates. All alkyl groups of the dye generally possess one to twelve carbon atoms. For the purpose of the present invention, the carboxylic group of the dye may or may not have a substituent on the alkyl carbon adjacent to the carboxyl group, which is neither reactive nor sterically hinders aminoacylation of the carboxylic group.

Of particular interest are the cyanine and related dyes. In one embodiment, the cyanine dyes, shown in FIG. 1 and discussed above, are used.

In accordance with the present invention, suitable reagents for forming at least one acyl fluoride group with a dye include, but are not limited to, carboxyl reactive fluorinating agents. In accordance with one embodiment of the present invention, a reagent may be diethylamino sulphur trifluoride (DAST) which reacts with carboxyl groups of cyanine dye in the following reaction exemplified by the reaction with Cy5:

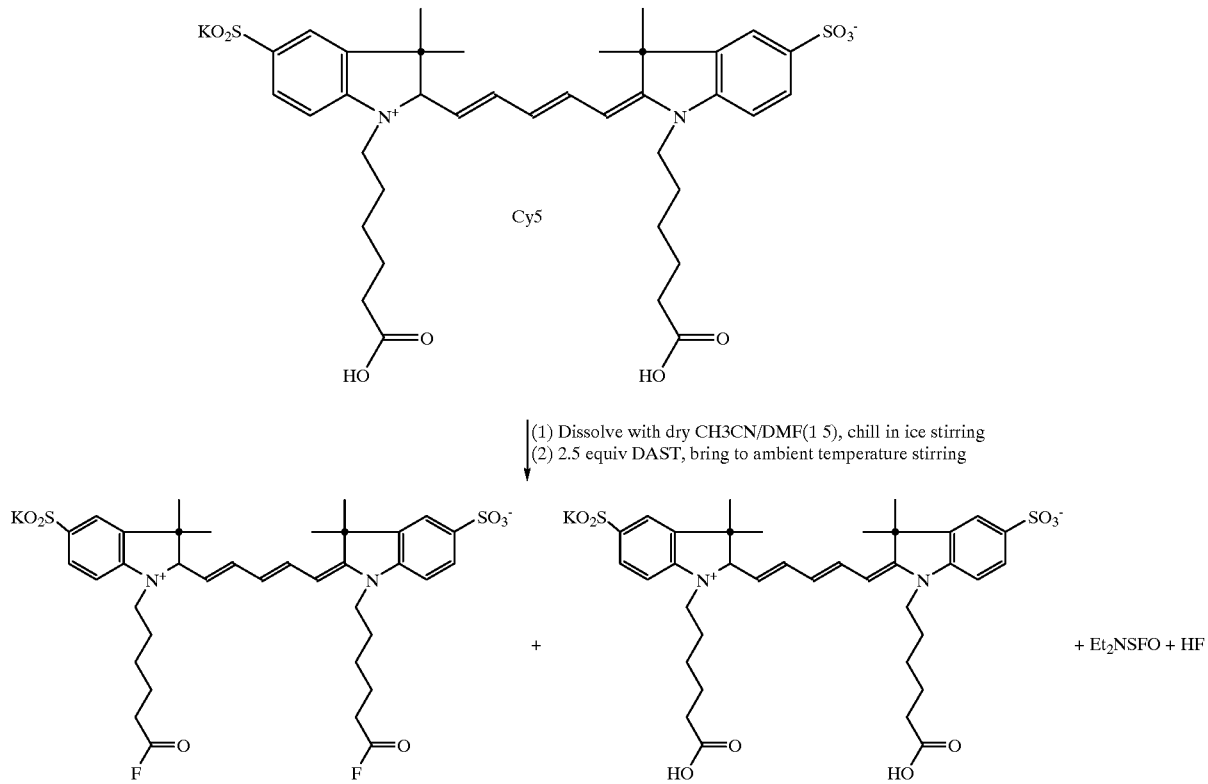

Cy5

(1) Dissolve with dry CH3CN/DMF(1 5), chill in ice stirring
(2) 2.5 equiv DAST, bring to ambient temperature stirring + Et$_2$NSFO + HF Other reagents include, but are not limited to, cyanuric fluoride:

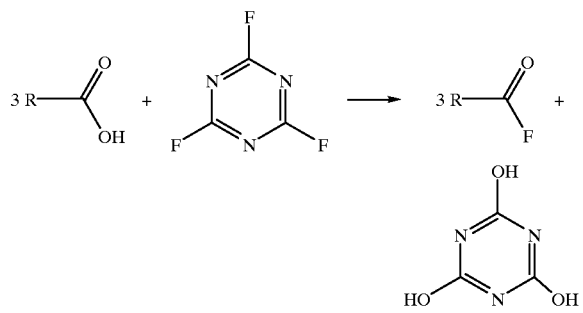

and tetramethylfluoroformadinium hexafluorophosphate (TFFH):

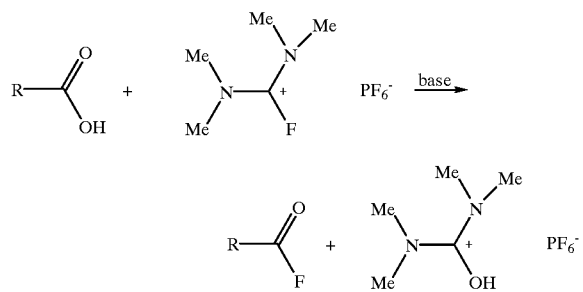

For the purpose of this invention a dye is reacted with a suitable fluorinating reagent under a condition that is sufficient to form a dye with at least one acyl fluoride group. In general, when reacting a dye with a fluorinating reagent, the amount of fluorinating reagent must be sufficient so that at least one acyl fluoride group is formed. In one embodiment, for example, the amount of DAST combined with the cyanine dye is greater than about 0.75 molar equivalents. When needed, an excess (for example, greater than about 2.5 molar equivalents) of DAST is combined with the cyanine dye to ensure that only diacyl fluoride species will be formed. The cyanine dye of the present invention may also be dissolved in a solvent prior to reacting with the fluorinating agent. Typically, the solvent comprises acetonitrile, dimethylformamide (DMF), or a 1:1 mixture thereof.

In one embodiment, the method for activating a dye further comprises an additional step of precipitating the activated dye from the mixture by filtering the reaction mixture into an excess (9x) of anhydrous diethyl ether. The obtained supernatant is further aerated with argon to initiate precipitation and displace dissolved air. After standing overnight and the addition of one additional volume of anhydrous diethyl ether, the supernatant is aspirated with argon and dried under vacuum. Further additional washing steps utilizing diethyl ether, hexane and other solvents do not assist purification and, therefore, can be omitted to improve yield and simplify the protocol.

Advantageously, it has been discovered that acyl (di) fluorides of cyanine dyes are completely soluble in water and react rapidly in aqueous conditions. The side product of their reaction with an amino group is a trace amount of hydrogen fluoride which is immediately neutralized in the aqueous buffer which is used as solvent or by an equivalent or two of a hindered organic base if the reaction is performed in non-aqueous conditions. The remaining acyl fluoride on the dye after reaction with an amino group is expected to be quenched by prolonged exposure, as compared to the initial reaction, to water in moderately basic buffered conditions. Despite their high reactivity, acyl (di)fluorides of cyanine dyes are surprisingly stable at ambient conditions and, when stored in a cool dry environment or under argon, have extended shelf lives. It is another advantage of the present invention that the preparation of the cyanine dye acyl (di)fluorides will consist of a simple one-step with minimal work-up to produce the activated cyanine dyes.

Another aspect of this invention provides a method of labeling biological and non-biological materials comprising the steps of:
(a) providing an activated dye with at least one acyl fluoride group;
(b) providing a material containing a nitrogen nucleophile; and
(c) reacting said dye with said material under a condition sufficient to couple the dye to the material.

For the purposes of the present invention, dyes of the following general formula can be used:

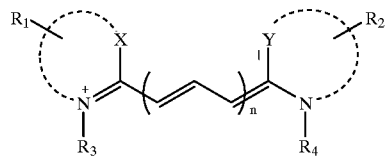

wherein:
each dotted line represents carbon atoms necessary to form a fused substituted or unsubstituted aromatic ring;
n is an integer selected from the group consisting of 1, 2 and 3;
X and Y are selected from the group consisting of S, O, N, $CH_2$ and $C(CH_3)_2$;
at least one of said $R_1$ and $R_2$ comprises a sulfonic acid or sulfonate group attached to the aromatic ring; and
$R_3$ and $R_4$ are independently selected from the group consisting of alkylcarboxylate, activated alkylcarboxylate and an inert group; wherein at least one of the $R_3$ and $R_4$ groups is alcylcarboxylate or activated alkylcarboxylate with carboxyl group converted to an acyl fluoride and wherein the inert group is a group that is inert towards acyl fluoride and has a sterical structure which allows aminoacylation of the acyl fluoride group. The inert group may be selected from the group consisting of alkanes, alkenes, dienes, alkynes, arenes, ketones, amides, and ethers. When necessary to improve stability, the alkyl carbon adjacent to the acyl fluoride group may also be substituted with a substituent group that is neither reactive nor sterically hinders aminoacylation.

The dyes can contain a heterocyclic ring, a single ring aromatic structure, such as a phenyl ring, or a fused ring structure, such as a naphthyl ring. While it is required that at least one $R_3$ or $R_4$ group is acyl fluoride, both $R_3$ and $R_4$ groups can be acyl fluorides. All alkyl and acyl groups of the dye generally possess one to twelve carbon atoms. In one embodiment, the activated dye is selected from the group consisting of cyanine and related dyes, for example, from the group of cyanine dyes shown in FIG. 1 and discussed above.

For the purpose of the present invention, materials suitable for labeling with acyl fluoride activated dyes can be biological or non-biological materials containing a nitrogen nucleophile. For example, biological materials can be cells, proteins, amino-modified nucleic acids, particularly oligonucleotides and their combinations. Examples of non-biological materials that contain nitrogen nucleophiles include, but are not limited to, polymers and polymeric particles.

In one embodiment, the amino-modified biological materials are amino-modified biopolymers, e.g. amino-modified oligonucleotides and peptides. For example, an amino-modified oligonucleotide having the following general structure can be labeled with acyl fluoride activated dyes:

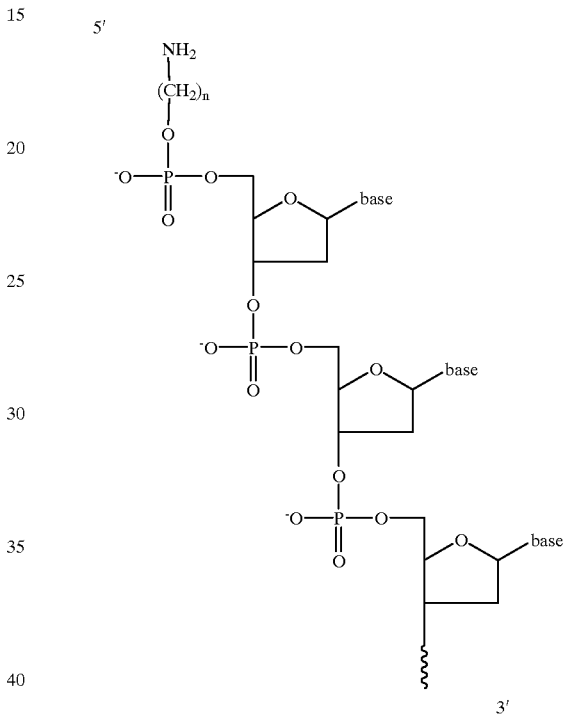

The amino-modified oligonucleotides are prepared by attaching a primary aliphatic amine to the 5' terminus of an oligonucleotide. Reagents and instructions for their use in attaching primary aliphatic amine to oligonucleotides are commercially available from Clontech Laboratories, Inc. of Palo Alto, Calif. (See Clontech Product Protocol, PR71095 "N-MMT-$C_n$—AminoModifiers".)

Those skilled in the art will appreciate that any number of sites on the oligonucleotide, in addition to its 5' end phosphate, can be selected to attach the amino group, including the base sites on the sugar moieties. Amino derivatized biopolymers provide an advantage of favorable reaction kinetics associated with the amide bond formation.

In accordance with the present invention, acyl fluoride of a cyanine dye is reacted with a nitrogen nucleophile-containing material under a condition sufficient to covalently bind (or couple) the dye to the material. The reaction of acyl fluoride functionalities of activated cyanine dye with the amino functionality of a biological or non-biological material results in formation of stable amide linkages as shown in the simplified reaction below:

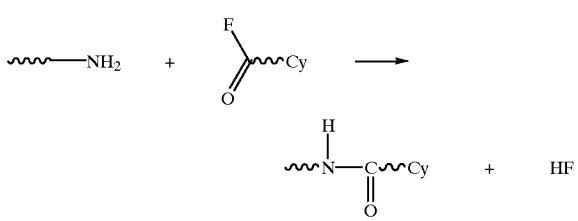

In the preferred embodiment, the activated dye is added in a molar excess as compared to the modified oligonucleotide.

The materials being labeled may be in a mixture including other materials. The mixture, in which the labeling reaction occurs, can be a liquid mixture, particularly a water mixture. In accordance with the present invention, the acyl fluoride activated cyanine dye may be reacted with a material containing a nitrogen nucleophile (or amino derivatized material) in the presence of an aqueous buffer, for example, a carbonate buffer. In one embodiment, a 5M potassium carbonate buffer containing about 10% (v/v) DMF is used. Bringing the acyl fluoride functionalities into contact with the amino group results in the displacement of the fluoride and the formation of an amide bond. The reaction between the acyl fluoride and amino group is rapid at room temperatures and will typically go to completion in a matter of seconds.

The labeled fragments of DNA or RNA can be used as fluorescent hybridization probes to identify the presence and quantity of specific complementary nucleotide sequences in samples containing DNA or RNA. Also, the dye can be attached to a hormone or ligand (such as a hormone, protein, peptide, lymphokine or metabolite) which in turn can be attached to a receptor. When the target is a type of cell, the present invention can be employed to measure the amount of labeled antibodies which are attached to that type of cell. The measurement can be made by determining the relative brightness or dimness of the luminescence of the cells. Detailed descriptions of these and many other possible applications of cyanine dye labels are provided in the pending U.S. application Ser. No. 09/100,150, entitled "Efficient Activated Cyanine Dyes," U.S. Pat. No. 5,627,027, entitled "Cyanine Dyes as Labeling Reagents for Detection of Biological and Other Materials by Luminescence Methods," U.S. Pat. No. 5,569,587, entitled "Method for Labeling and Detecting Materials Employing Luminescent Arylsulfonate Cyanine Dyes," the relevant contents of which are incorporated herein by reference.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

EXAMPLE 1

Synthesis of Acyl Fluoride of Cy5 Cyanine Dye

Acyl Fluoride of Cy5 cyanine dye was obtained using the following procedure. 1.70 g of the potassium salt of Cy5 (FW=780.9; synthesized by the method of S. R. Mujumder et al., *Bioconjugate Chemistry*, 4(2):105 (1993) and 7(2):356 (1996)) were suspended in 40 ml of dry dimethylformamide (over 4A sieve), stirred to dissolve and cooled on ice. An excess (greater than 1.5 mequiv.) of diethylamino- sulfur trifluoride (DAST; FW=161.9) was added with stirring for 1 h in ice. 2 ml aliquots of the reaction mixture were added to 48 ml of chilled anhydrous diethyl ether in polypropylene centrifuge tubes to form a blue precipitate. After 10 min of centrifugation at 2500 rpm, the diethyl ether was decanted so that the precipitates could be redissolved in a minimal volume of dry dimethylformamide and pooled. The pool was re-precipitated with 2 volumes of diethyl ether and centrifuged again. This washing process was repeated one more time before the resultant blue product was dried under vacuum overnight. A quantitative crude yield was obtained. The product was stored under dry argon gas at −20EC.

The acyl fluoride of Cy5 cyanine dye was also prepared by this method substituting dry acetonitrile (over 3A sieve) for dimethylformamide as the solvent. A crude yield of 95.9% was obtained in this latter case.

Product Analysis

For product analysis, the activated product and Cy5 cyanine dye standard (unmodified) were dissolved in an excess of methanol. It was expected that, as a result of this step, acyl fluoride species would be converted to their methyl esters. The obtained solutions were subjected to Thin Layer Chromatography (TLC).

Equal aliquots of the activated dye and standard dye solutions were spotted on a thin-layer plate (60/254 nm silica gel coated on a glass support) at an equal distance from the edge of the plate. The chromatogram was developed with dichloromethane/methanol (2:1) solvent mixture. Because the components of the mixture are dyes, the developed-"spots" were visible to the eye and did not require any spot-visualizing techniques (used for non-colored substances). The reported retention factor (Rf) values were calculated by the following equation:

Rf=(distance the spot moves)/(distance to the solvent front).

Results and Conclusions

Figure 2:
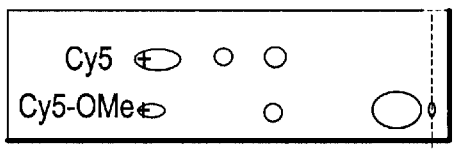
FIG. 2 shows a thin layer chromatogram of Cy5 fluorinated with excess (greater than 2.5 mequiv) of the fluorinating agent (DAST) and then reacted with excess methanol.

FIG. 2 shows the obtained thin layer chromatogram, which reveals the presence of a species migrating faster (Rf=0.84) than standard Cy5 (Rf=0.15). This species was concluded to represent the dimethyl ester of the diacyl fluoride form of Cy5. Concern was retained as to the stability of the sulphonate groups to DAST while blocked as the potassium salt. The precipitated material, however, remained soluble in water, suggesting the retention of the salt formed after the fluorination of the carboxyl group(s) in Cy5.

EXAMPLE 2

Synthesis of Acyl Fluoride of Cy5 Cyanine Dye

Acyl fluoride of Cy5 cyanine was obtained using the following procedure. One hundred six milligrams of the potassium salt of Cy5 were suspended in 10 ml of dry acetonitrile and cooled on ice while stirring under argon. After 30 min., 0.75 mequiv DAST (about 0.204 mmol, 27 µl) was added with stirring. After 5 min. at 0° C., the reaction mixture was warmed to ambient temperature and 10% (v/v) of dry DMF was added. The reaction was allowed to continue for a further 10 min. before filtering through a coarse glass sinter into 250 ml of anhydrous diethyl ether. Argon was then bubbled through the solution of acyl fluoride cyanine dye in diethyl ether to initiate precipitation and displace dissolved air. The formed precipitate was allowed to settle overnight. The next day, additional anhydrous diethyl ether was added to the supernatant (1:1 v/v), the precipitate was allowed to settle and the supernatant was aspirated.

Product Purification and Analysis

The settled precipitate was dissolved in 30 ml of dry DMF. The solution was distributed to six 50 ml centrifuge tubes and precipitated by low speed centrifugation at 2500 rpm for 10 min. The supernatant was removed and the precipitate was resuspended in anhydrous diethyl ether. Then, the washing steps were repeated with dry hexane (over 3Å sieve) and anhydrous ether. The precipitate was dried under a stream of argon. A crude yield of 62.1 mg (corresponding to 57.4%) was calculated. TLC was used to analyze the obtained product as described in detail in Example 1.

Results and Conclusions

Figure 3:
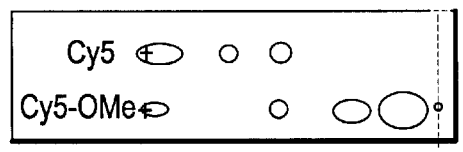
FIG. 3 shows a thin layer chromatogram of fluorinated Cy5, when less than 1:1 molar ratio of the fluorinating agent (DAST) to the cyanine dye was used prior to reaction with excess methanol.

FIG. 3 shows the obtained thin layer chromatogram, which reveals the expected two fast migrating spots compared to the standard unmodified Cy5 cyanine dye. The species at Rf=0.84 is again concluded to be difluoride of Cy5 and that at Rf=0.65 to be the anticipated monoflouride of Cy5. It is apparent from Examples 1 and 2 that when less than 1:1 molar ratio of fluorinating agent to cyanine dye is used, both difluoride and monofluoride species are obtained, while molar excess of the fluorinating agent leads to formation of only difluoride species.

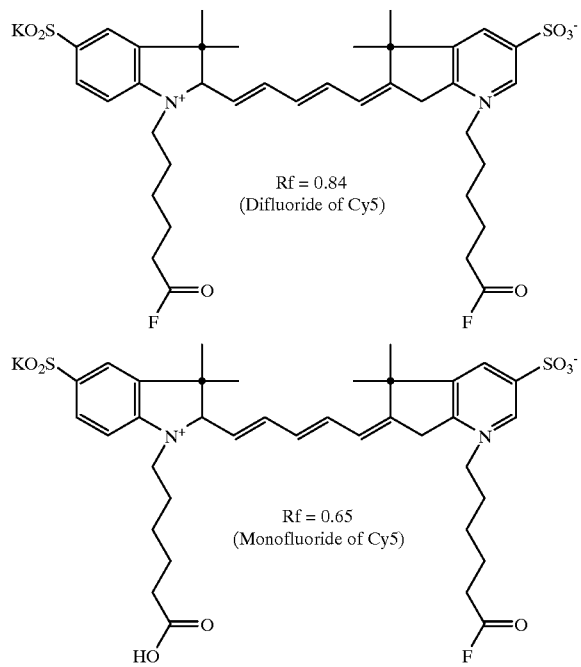

The crude product was again fully water soluble and, even after standing overnight in water or dilute base (addition of 10 μ sodium hydroxide), there was no change in the thin layer chromatogram observed.

EXAMPLE 3

Labeling of Amino-Oligonucleotide

Figure 4:
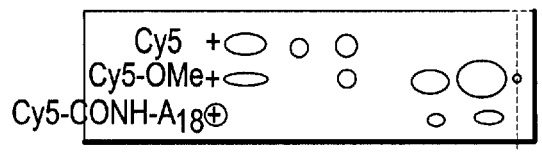
FIG. 4 shows a thin layer chromatogram of amino-oligonucleotide labeled with acyl fluoride-Cy5.

The dried product obtained as described in Example 2 above was dissolved in 40 μl of a solution of the amino- oligonucleotide, 5-$H_2N$-$A_{18}$-3', in 5 M potassium carbonate containing 10% (v/v) DMF. TLC of the obtained solution revealed a new species on the thin layer chromatogram which did not migrate from the origin (FIG. 4). The obtained product was concluded to be the covalently labeled Cy5-CONH-oligonucleotide product.

EXAMPLE 4

Labeling of Amino-Oligonucleotide

Short wild type (w/t) H-ras oligonucleotide sequence was purchased from Genosys Biotechnologies, Inc. and its 5' terminus was amino derivatized with N-MMT-$C_{12}$ Amino-Modifier cyanoethyl phosphoramidites from Clontech Laboratories according to the manufacturer's directions. The following amino derivatized sequence was obtained:

5'$H_2N$-CCGGCGGTGT-3'.

Figure 5:
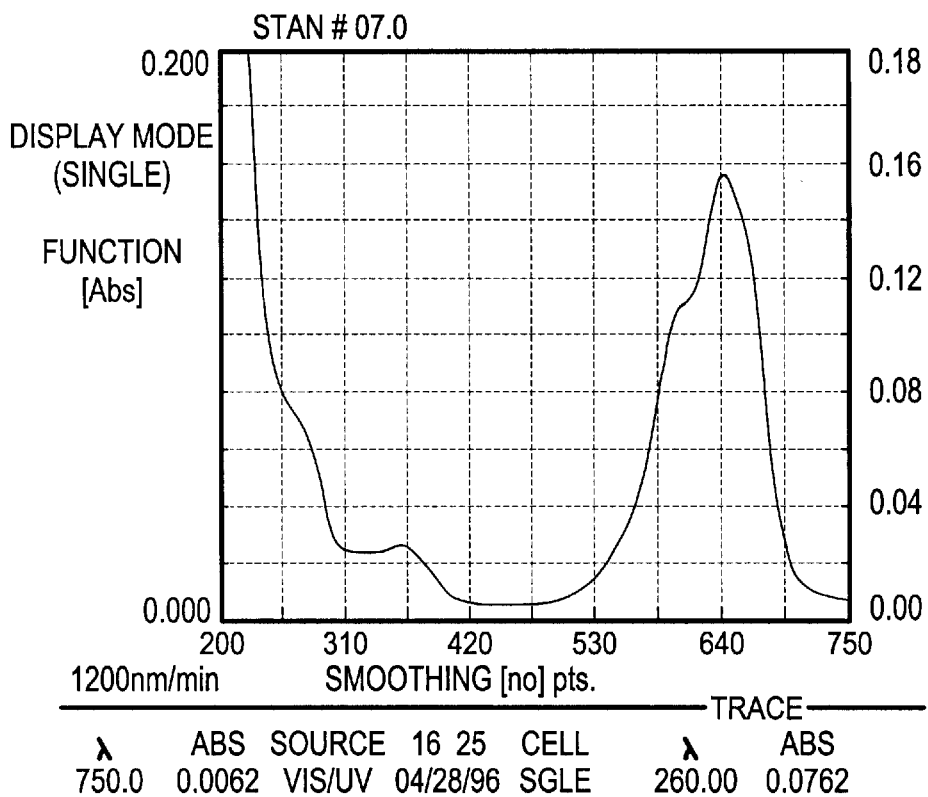
FIG. 5 shows a UV spectra of the labeled oligonucleotide purified on a Vistra fluorescence purification column.

To produce a sufficient quantity of the labeled oligonucleotide, an excess, >30 nmol (about 0.024 mg), of the crude precipitate product obtained as described in Example 2 was mixed with 3 nmol of H-ras w/t amino-oligonucleotide in 50 mM sodium phosphate buffer (pH 8.0), applied to a pre-spun Vistra fluorescence purification column (RRN#5757, manufactured by Amersham Pharmacia Biotech) and centrifuged at low speed. The blue eluant was then reapplied to another pre-spun purification column and recentrifuged to ensure the best separation of the oligonucleotide species and free Cy5. Again, a blue eluant was obtained. UV analysis of the eluant revealed the expected 260 nm and 640 nm maxima corresponding to the DNA and Cy5 components of the labeled oligonucleotide (FIG. 5).

EXAMPLE 5

Capillary Zone Electrophoresis of the Labeling Products

Figure 6:
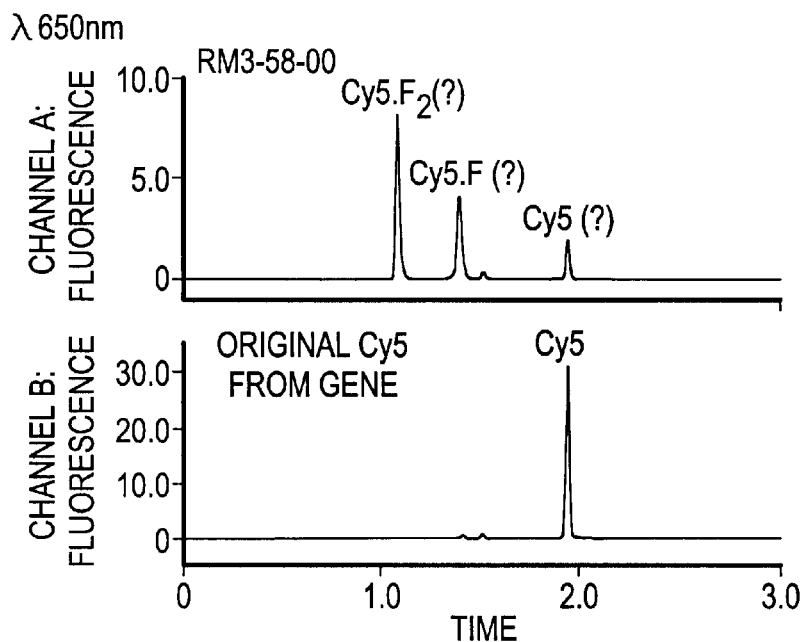
FIG. 6 shows an electropheragram of the crude fluorinated product of Cy5.

Capillary zone electrophoresis of the crude precipitated product obtained as described in Example 2 above revealed three major peaks (FIG. 6). The smallest peak had the same retention time as the starting material, Cy5. Deduced from the thin layer chromatogram, the largest peak was concluded to be the diacyl fluoride and the intermediate peak was concluded to be the monofluoride species.

Figure 7:
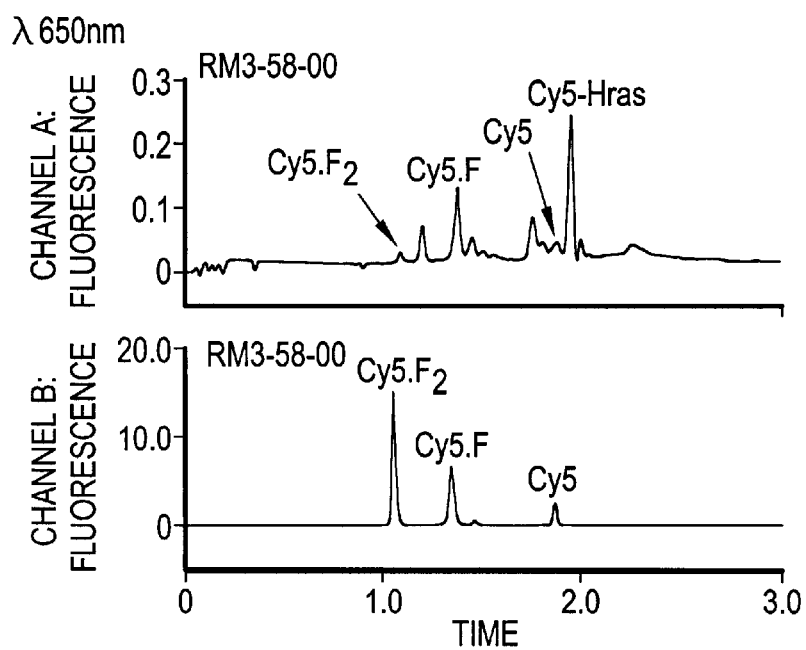
FIG. 7 shows an electropheragram of the Vistra column purified Cy5-labeled oligonucleotide.

Similarly, capillary zone electrophoresis of the Vistra column purified Cy5—CONH-oligonucleotide (FIG. 7) revealed a major peak unseen in the electropheragram of the fluorinated products. Noticeably, the Cy5 diacyl fluoride peak was more depleted than the monofluoride peak. It was, however, unclear whether this indicated preferential usage of diacyl fluoride during labeling or this was merely an artifact of the purification step. The electropheragrams were monitored at 650 nm to detect only Cy5 or Cy5-containing species.

EXAMPLE 6

Additional Purification of Oligonucleotide Labeling Product

In view of the remaining presence of fluorinated Cy5 species after the Vistra column purification step, 100 μl of this eluant was applied to a 26×1 cm G-25 Sephadex exclusion column and was eluted with 50 mM sodium phosphate buffer (pH 8.0). Fractions were collected from the first emergence of blue color in the eluant and optical densities (OD) were measured at 260 nm and 650 nm by UV-spectrometer (Beckman DU-70 spectrometer).

Results and Conclusions

Figure 8:
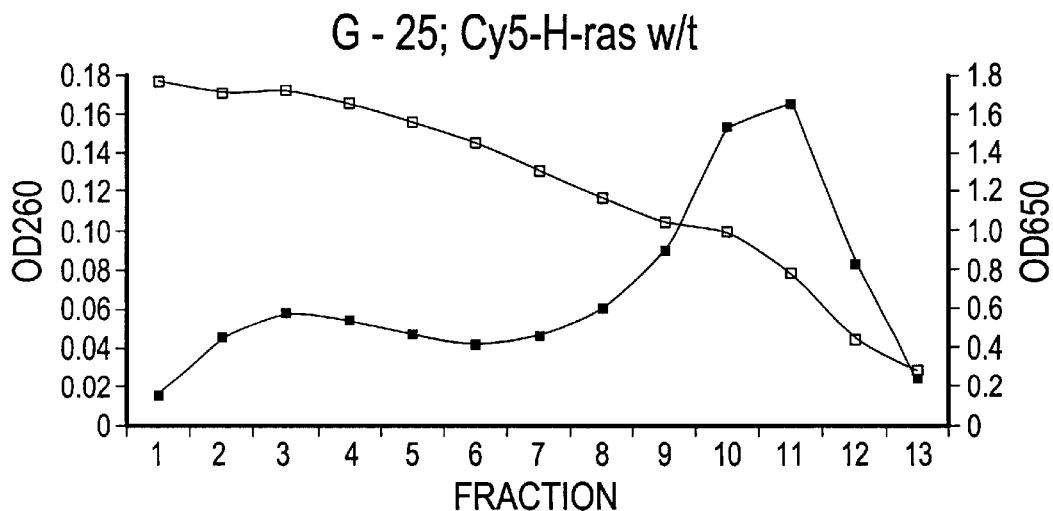
FIG. 8 shows optical density (at 260 nm and 650 nm) of eluents obtained by washing Cy5-labeled oligonucleotide on a 26×1 cm G-25 Sephadex exclusion column with sodium phosphate buffer.
Figure 9:
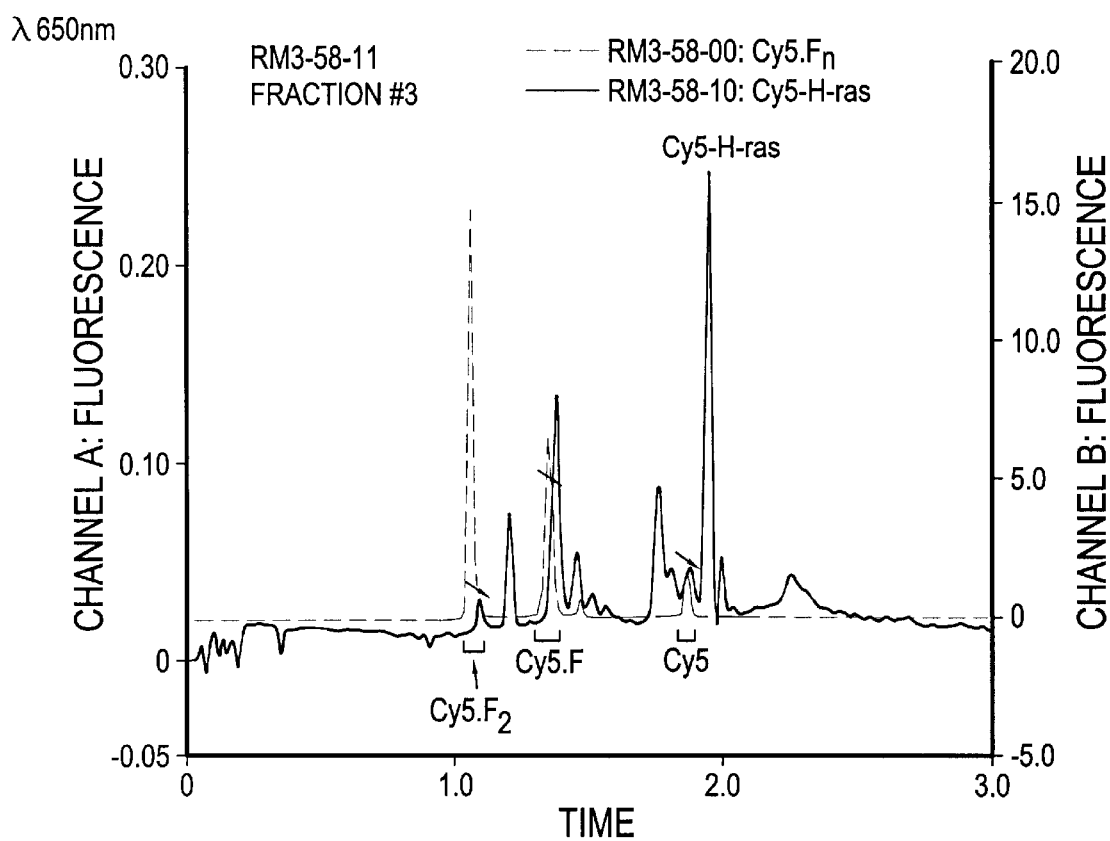
FIG. 9 shows an electropheragram of the Cy5-labeled oligonucleotide purified first on a Vistra column, and then on a G-25 Sephadex exclusion column.

The emergence of oligonucleotide and dye together in the void volume (FIG. 8) suggests as does the capillary zone electrophoresis, that the oligonucleotide was successfully covalently labeled with Cy5. However, this further purification step did not improve the electropheragram profile as shown in FIG. 9. Therefore, additional washing steps utilizing diethyl ether, hexane and other solvents did not seem to assist purification and can be abandoned to improve yield and to simplify the protocol.

EXAMPLE 7

Hybridization of Dye-Labeled H-ras with its Biotinylated Target

This example, schematically outlined below, is an additional demonstration of attachment of fluorinated Cy5 to H-ras oligonucleotide.

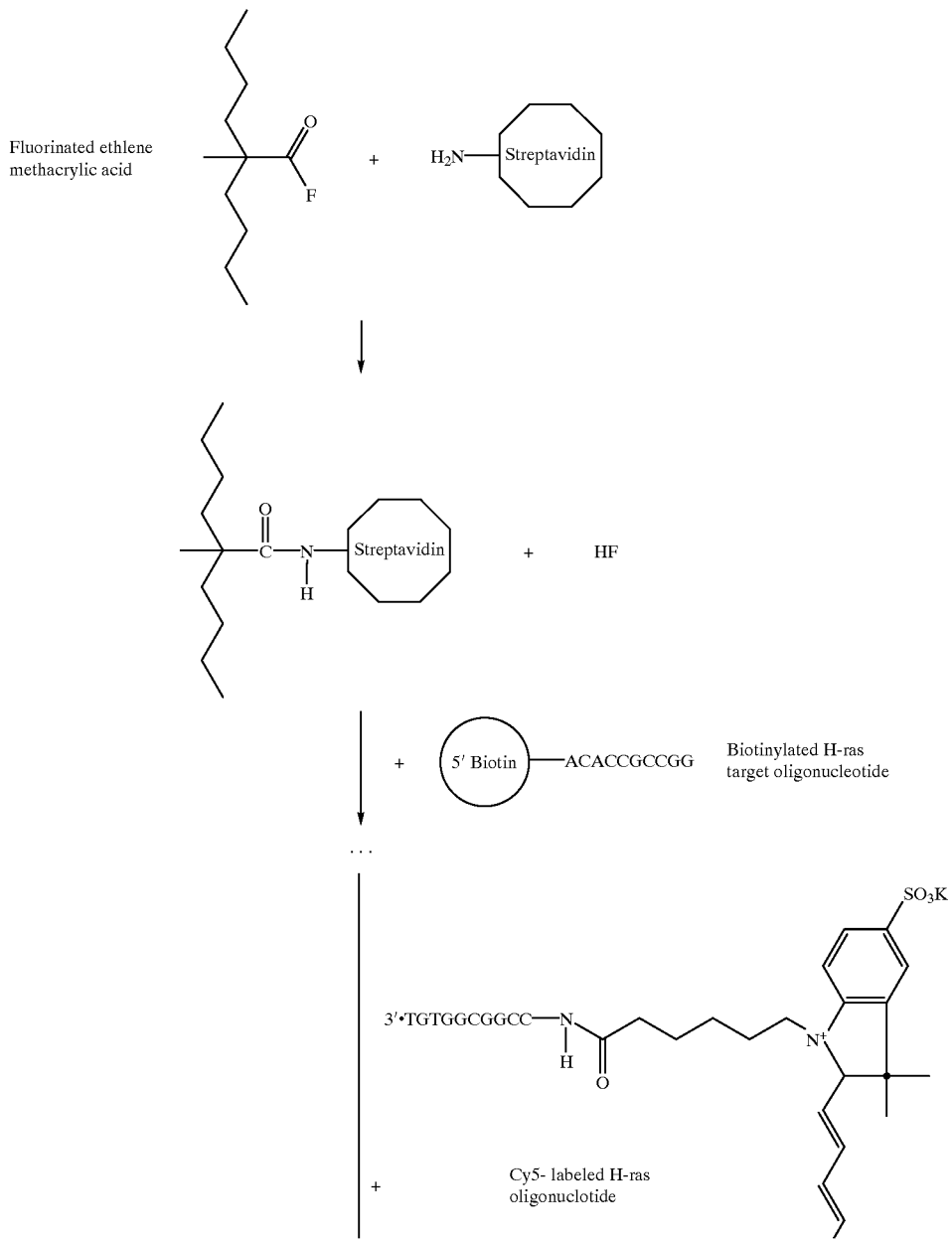

-continued

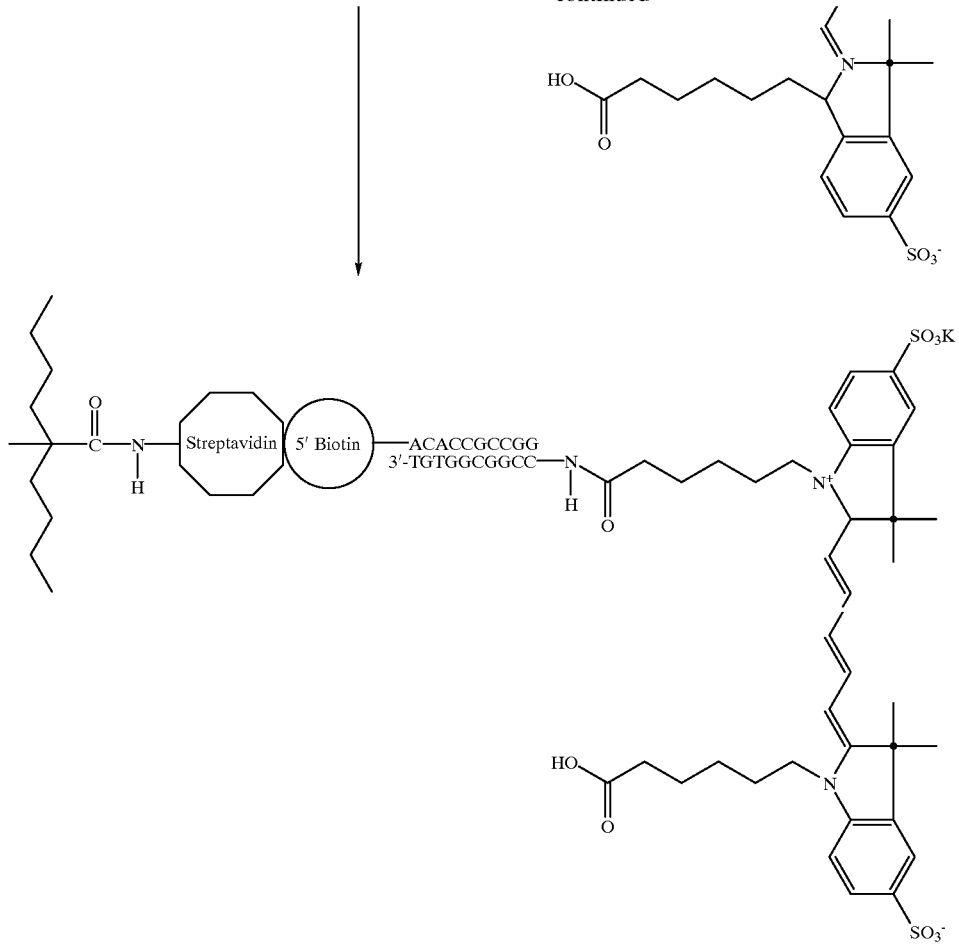

The oligonucleotide sequence complementary to the H-ras w/t sequence (H-ras target) was synthesized and biotinulated at their 5' ends utilizing the Clontech Biotin-ON™ Phosphoramidite Product Protocol #PR71093. The following sequence was obtained: 3'-GGCCGCCACA-BIOTIN-5'.

Figure 10:
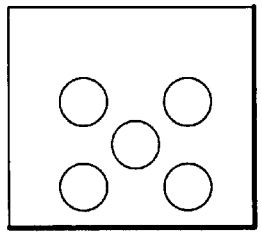
FIG. 10 shows the pattern in which Steptavidin was anchored to the fluorinated ethylene methacrylic acid copolymer.

The protein Streptavidin was anchored to a fluorinated ethylene methacrylic acid copolymer in a pattern, as shown on FIG. 10. After blocking the remaining unreacted surface with bovine serum albumin and washing with 0.1% Tween 20 in 2×SSPE buffer, the biotinylated target H-ras oligonucleotide sequence was allowed to bind specifically to the streptavidin. The copolymer surface was washed thoroughly with 2×SSPE buffer prior to incubation with the Cy5-labelled H-ras oligonucleotide (dissolved in an arbitrary volume of 2×SSPE buffer).

Figure 11:
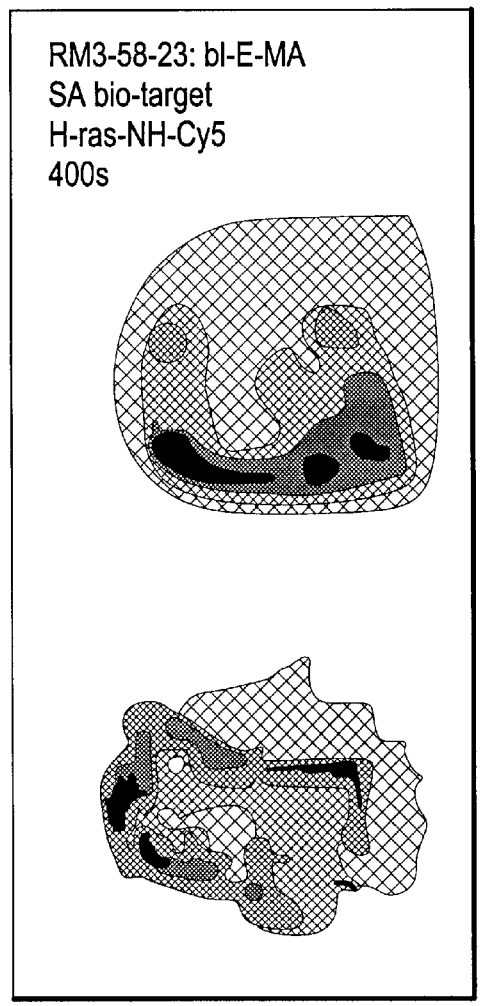
FIG. 11 shows the hybridization results of the biotinylated H-ras target with Cy5-labeled H-ras.

A non-specific binding control was run in parallel with the biotinylated H-ras target oligonucleotide replaced by a K-ras target (3'-CGACCACCGCAT-BIOTIN-5'). The squares of ethylene methacrylic acid copolymer were viewed in 2×SSPE, after washing, using a 640 nm source. Apart from reflections from the overlaying liquid, the pattern of five fluorescent spots was observed on the upper test square (FIG. 11). The presence of the specific pattern of fluorescent spots on the test, but not the control, was concluded to show that the H-ras oligonucleotide was indeed labeled with Cy5.

What is claimed is:

1. An activated dye having a formula:

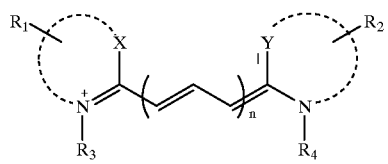

wherein:
each dotted line represents carbon atoms necessary to form a fused substituted or unsubstituted aromatic ring;
n is an integer selected from the group consisting of 1, 2 and 3;
X and Y are selected from the group consisting of S, O, N, $CH_2$ and $C(CH_3)_2$;
at least one of said $R_1$ and $R_2$ comprises a sulfonic acid or sulfonate group attached to the aromatic ring; and
$R_3$ and $R_4$ are independently selected from the group consisting of alkylcarboxylate, activated alkylcarboxylate and an inert group; wherein at least one of said $R_3$ and $R_4$ groups is alcylcarboxylate or activated alkylcarboxylate with a carboxyl group converted to an acyl fluoride, and wherein said inert group is a group that is inert towards acyl fluoride and has a sterical structure which allows aminoacylation of the acyl fluoride group.

2. The activated dye of claim 1, wherein said aromatic ring is phenyl, naphthyl, or heterocyclic ring.

3. The activated dye of claim 1, wherein both $R_3$ and $R_4$ are acyl fluorides.

4. The activated dye of claim 1, wherein the inert group is selected from the group consisting of alkanes, alkenes, dienes, alkynes, arenes, ketones, amides, and ethers.

5. The activated dye of claim 1, wherein said alkyls possess 1 to 12 carbon atoms.

6. The activated dye of claim 1, wherein one or both $R_3$ and $R_4$ have a substituent group on the alkylcarbon adjacent to the acyl fluoride which is inert towards the acyl fluoride and has a sterical structure that permits aminoacylation of the acyl fluoride group.

7. The activated dye of claim 1, wherein said dye is a cyanine dye.

8. The activated dye of claim 7, wherein said cyanine dye is selected from the group consisting of Cy5, benzyl Cy5, dibenzyl Cy5, Cy7, benzyl Cy7 and dibenzyl Cy7.

9. The activated dye of claim 1, wherein said dye is selective towards nitrogen nucleophiles over competing species.

10. The activated dye of claim 9, wherein said competing species are oxygen nucleophiles.

11. The activated dye of claim 1, wherein said dye is soluble in aqueous solutions.

12. A method for activating a dye comprising the steps of:
 (a) providing a dye having at least one carboxylic group;
 (b) providing a fluorinating reagent capable of reacting with the carboxylic group of said dye to form acyl fluoride; and
 (c) reacting said dye with said fluorinating agent under a condition sufficient to form a dye with at least one acyl fluoride group,
 wherein said dye has a structure:

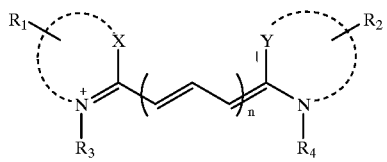

wherein:
 each dotted line represents carbon atoms necessary to form a fused substituted or unsubstituted aromatic ring;
 n is an integer selected from the group consisting of 1, 2 and 3;
 X and Y are selected from the group consisting of S, O, N, $CH_2$ and $C(CH_3)_2$;
 at least one of said $R_1$ and $R_2$ comprises a sulfonic acid or sulfonate group attached to the aromatic ring; and
 $R_3$ and $R_4$ are independently selected from the group consisting of alkylcarboxylate, activated alkylcarboxylate and an inert group; wherein at least one of said $R_3$ and
 $R_4$ groups is alcylcarboxylate or activated alkylcarboxylate with a carboxyl group converted to an acyl fluoride and wherein said inert group is a group that is inert towards acyl fluoride and has a sterical structure which allows aminoacylation of the acyl fluoride group.

13. The method of claim 12, wherein said aromatic ring is phenyl, naphthyl, or heterocyclic ring.

14. The method of claim 12, wherein both $R_3$ and $R_4$ are alkylcarboxylates.

15. The method of claim 12, wherein the inert group is selected from the group consisting of alkanes, alkenes, dienes, alkynes, arenes, ketones, amides, and ethers.

16. The method of claim 12, wherein one or both $R_3$ and $R_4$ have a substituent group on the alkylcarbon adjacent to the acyl fluoride which is inert towards and has a sterical structure that permits aminoacylation of the acyl fluoride group.

17. The method of claim 12, wherein said alkyls possess 1 to 12 carbon atoms.

18. The method of claim 12, wherein said dye is a cyanine dye.

19. The method of claim 18, wherein said cyanine dye is selected from the group consisting of Cy5, benzyl Cy5, dibenzyl Cy5, Cy7, benzyl Cy7 and dibenzyl Cy7.

20. A method for activating a dye comprising the steps of:
 (a) providing a dye having at least one carboxylic group;
 (b) providing a fluorinating reagent selected from the group consisting of diethylaminosulfur trifluoride (DAST), cyanuric fluoride and tetramethylfluoroformadinium hexafluorophosphate (TFFH); and
 (c) reacting said dye with said fluorinating agent under a condition sufficient to form a dye with at least one acyl fluoride group.

21. The method of claim 20, wherein said fluorinating agent is DAST.

22. The method of claim 21, wherein said amount of DAST combined with said cyanine dye is greater than about 0.75 molar equivalents.

23. The method of claim 22, wherein said amount of DAST combined with said cyanine dye is greater than about 1.5 molar equivalents.

24. The method of claim 20, wherein said dye is dissolved in a solvent prior to reacting with the fluorinating agent.

25. The method of claim 24, wherein the solvent is acetonitrile, DMF, or a mixture thereof.

26. The method of claim 20, further comprising an additional step of precipitating the activated dye from the mixture.

27. The method of claim 26, wherein the activated dye is precipitated by adding diethyl ether.

28. A method of labeling biological and non-biological materials comprising the steps of:
 (a) providing an activated dye with at least one acyl fluoride group;
 (b) providing a material containing a nitrogen nucleophile; and
 (c) reacting said dye with said material under a condition sufficient to couple the dye to the material,
 wherein said dye has a structure:

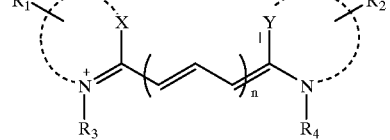

wherein:
 each dotted line represents carbon atoms necessary to form a fused substituted or unsubstituted aromatic ring;
 n is an integer selected from the group consisting of 1, 2 and 3;
 X and Y are selected from the group consisting of S, O, N, $CH_2$ and $C(CH_3)_2$;

at least one of said $R_1$ and $R_2$ comprises a sulfonic acid or sulfonate group attached to the aromatic ring; and $R_3$ and $R_4$ are independently selected from the group consisting of alkylcarboxylate, activated alkylcarboxylate and an inert group; wherein at least one of said $R_3$ and $R_4$ groups is alcylcarboxylate or activated alkylcarboxylate with carboxyl group converted to an acyl fluoride and wherein said inert group is a group that is inert towards acyl fluoride and has a sterical structure which allows aminoacylation of the acyl fluoride group.

29. The method of claim 28, wherein said biological material is selected from the group consisting of proteins, cells, amino-modified nucleic acids and combinations thereof.

30. A method of labeling amino-modified oligonucleotides comprising the steps of:

(a) providing an activated dye with at least one acyl fluoride group;

(b) providing an amino-modified oligonucleotide; and (c) reacting said dye with said amino-modified oligonucleotide under a condition sufficient to couple the dye to the amino-modified oligonucleotide.

31. The method of claim 28, wherein said non-biological materials are polymers.

32. The method of claim 28, wherein said aromatic ring is phenyl, naphthyl, or heterocyclic ring.

33. The method of claim 28, wherein both $R_3$ and $R_4$ are acyl fluorides.

34. The method of claim 28, wherein the inert group is selected from the group consisting of alkanes, alkenes, dienes, alkynes, arenes, ketones, amides, ethers.

35. The method of claim 28, wherein said alkyls possess 1 to 12 carbon atoms.

36. The method of claim 28, wherein one or both $R_3$ and $R_4$ have a substituent group on the alkylcarbon adjacent to the acyl fluoride which is inert towards the acyl fluoride and has a sterical structure that permits aminoacylation of the acyl fluoride group.

37. The method of claim 28, wherein said dye is a cyanine dye.

38. The method of claim 37, wherein said cyanine dye is selected from the group consisting of Cy5, benzyl Cy5, dibenzyl Cy5, Cy7, benzyl Cy7 and dibenzyl Cy7.

39. The method of claim 30, wherein said activated dye is added in a molar excess as compared to the amino-modified oligonucleotide.

* * * * *